United States Patent
Paine et al.

(10) Patent No.: US 8,290,573 B2
(45) Date of Patent: Oct. 16, 2012

(54) SYSTEMS AND METHODS FOR QUANTIFYING AND PROVIDING INDICIA OF ST-SEGMENT RESOLUTION IN AN ECG SIGNAL

(75) Inventors: Diane S. Paine, Redmond, WA (US); Daniel J. Wilson, Sammamish, WA (US)

(73) Assignee: MR Holdings (HK) Limited, Hong Kong (CN)

( * ) Notice: Subject to any disclaimer, the term of this patent is extended or adjusted under 35 U.S.C. 154(b) by 546 days.

(21) Appl. No.: 12/544,811

(22) Filed: Aug. 20, 2009

(65) Prior Publication Data
US 2010/0049067 A1    Feb. 25, 2010

Related U.S. Application Data

(60) Provisional application No. 61/090,789, filed on Aug. 21, 2008.

(51) Int. Cl.
*A61B 5/0452* (2006.01)
(52) U.S. Cl. ...................................................... 600/509
(58) Field of Classification Search .................. 600/509, 600/516, 517
See application file for complete search history.

(56) References Cited

U.S. PATENT DOCUMENTS

2001/0025139 A1*   9/2001   Pearlman ...................... 600/301

\* cited by examiner

*Primary Examiner* — Eric D. Bertram
(74) *Attorney, Agent, or Firm* — Kory D. Christensen; Stoel Rives LLP

(57) ABSTRACT

Systems and methods are provided for quantifying and providing indicia of ST-segment resolution in an electrocardiogram (ECG) signal. A receiver acquires an electrocardiogram (ECG) signal that includes an ST-segment. A processor processes the ECG signal to determine values for the ST-segment deviation relative to an isoelectric baseline. A user is allowed to provide a baseline signal to the processor. The processor responds to the baseline signal by marking a baseline ST-segment value corresponding to a baseline time. A user interface displays a linear graphical trend of variations in the measured ST-segment values relative to the baseline ST-segment value. In certain embodiments, the processor detects user-selected trigger events such as post-intervention ST deviation relative to the baseline time and the baseline ST-segment value, and provides indicia of the trigger event. In addition, or in other embodiments, a verbal annunciation of a percent ST-segment resolution is provided.

14 Claims, 8 Drawing Sheets

ST Elevation

ST Depression

| % ST-Segment Resolution (From Baseline/Post-Intervention) | | | | |
|---|---|---|---|---|
| ECG Lead | 30 Minutes | 60 Minutes | 90 Minutes | 180 Minutes |
| Lead II | 20% | 54% | 65% | 70% |
| Lead III | 18% | 40% | 60% | 75% |
| Lead AVF | 15% | 35% | 50% | 65% |

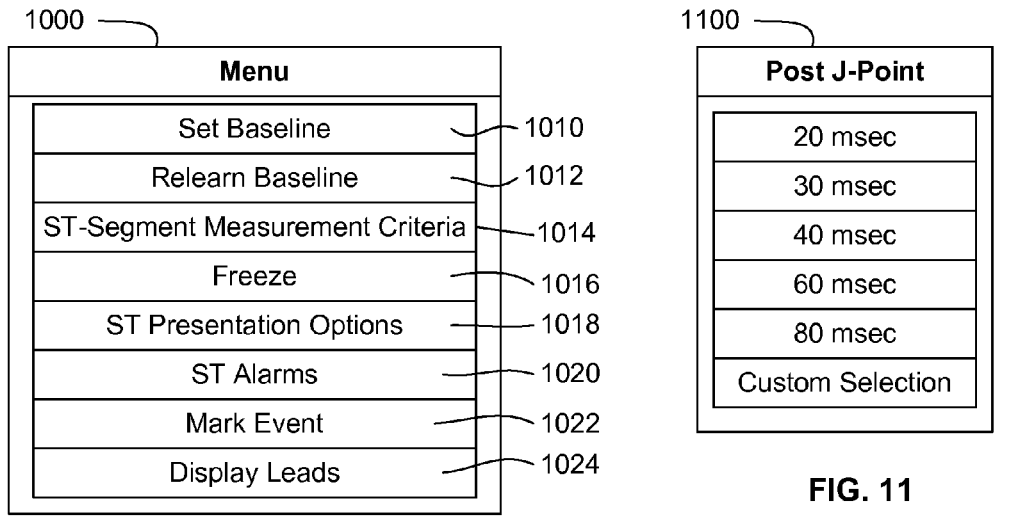
FIG. 10
FIG. 11
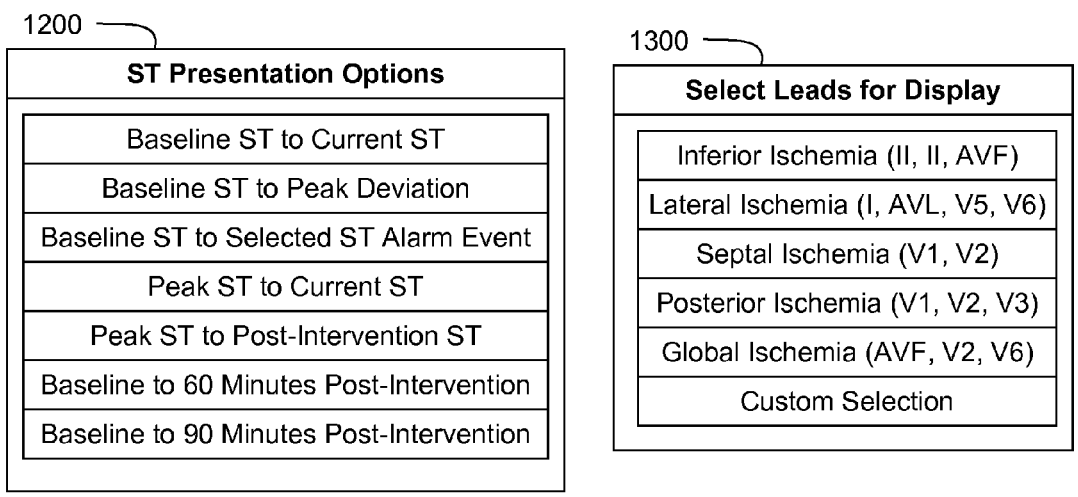
FIG. 12
FIG. 13

US 8,290,573 B2

SYSTEMS AND METHODS FOR QUANTIFYING AND PROVIDING INDICIA OF ST-SEGMENT RESOLUTION IN AN ECG SIGNAL

CROSS-REFERENCE TO RELATED APPLICATIONS

This application claims the benefit of U.S. Provisional Application No. 61/090,789, filed Aug. 21, 2008, which is incorporated herein by reference.

TECHNICAL FIELD

This disclosure generally relates to cardiac analysis.

SUMMARY

Systems and methods are provided for quantifying and providing indicia of ST-segment resolution in an electrocardiogram (ECG) signal. In one embodiment, a receiver acquires an ECG signal through a plurality of leads. The ECG signal includes, for each of a plurality of detected heart beats, an ST-segment between a QRS complex and a T wave. A processor processes the ECG signal to determine values for the ST-segment relative to an isoelectric value. One or more controls provide a user selected baseline signal to the processor. The processor responds to the baseline signal by marking a baseline ST-segment value corresponding to a baseline time. A user interface in communication with the processor displays a linear graphical trend of variations in the measured ST-segment values relative to the baseline ST-segment value. In certain embodiments, the processor detects a trigger event relative to at least one of the baseline time and the baseline ST-segment value, and provides indicia of the trigger event. In addition, or in other embodiments, a verbal annunciation of a percent ST-segment resolution is provided.

Additional aspects and advantages will be apparent from the following detailed description of preferred embodiments, which proceeds with reference to the accompanying drawings.

BRIEF DESCRIPTION OF THE DRAWINGS

FIG. 10 graphically illustrates a user menu interface usable with the system shown in FIG. 3 according to one embodiment;

FIG. 11 graphically illustrates a user menu for selecting a post J-point value according to one embodiment;

FIG. 12 graphically illustrates a user menu for selecting ST presentation options according to one embodiment; and FIG. 13 graphically illustrates a user menu for selecting groups of leads for display according to one embodiment.

DETAILED DESCRIPTION

Figure 1:
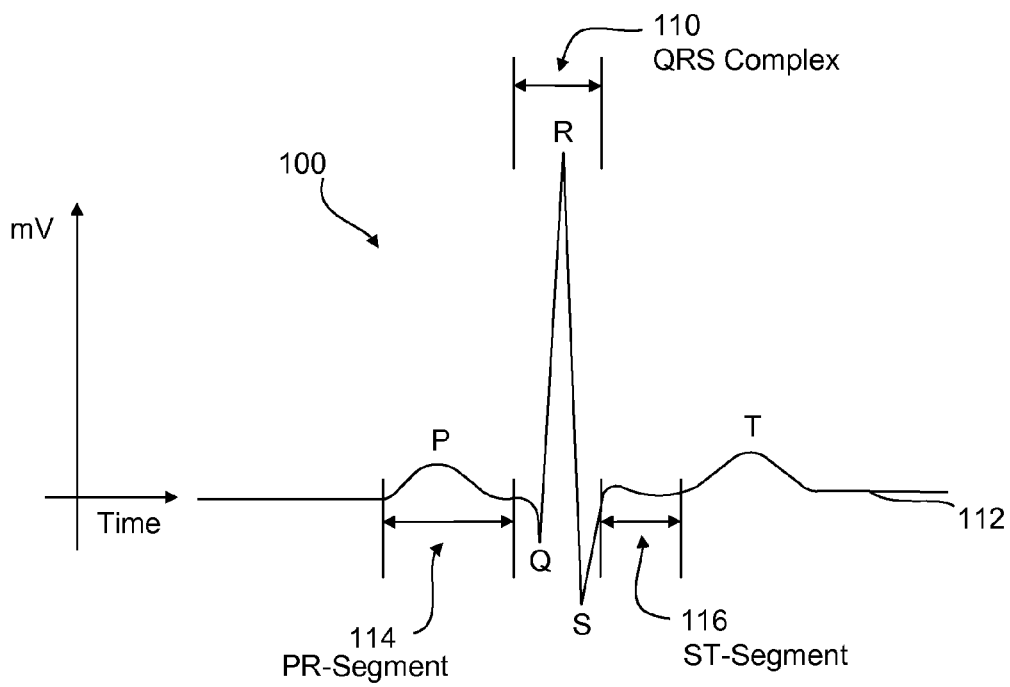
FIG. 1 graphically represents a typical ECG signal of a heart of a normal, healthy person and includes a P wave, a Q wave, an R wave, an S wave, and a T wave.

Electrical waves cause the heart muscle to pump. These waves pass through the body and may be measured using electrodes attached to a patient's skin. Electrodes on different sides of the heart measure the activity of different parts of the heart muscle. An electrocardiogram (ECG) displays voltages between pairs of electrodes (leads) from different directions. Thus, an ECG may be used to display an overall rhythm of the heart and weaknesses in different parts of the heart muscle.

ECGs are used to measure and diagnose abnormal rhythms of the heart, including abnormal rhythms caused by damage to the conductive tissue that carries electrical signals. The ECG may be measured using various lead systems. Generally, the ECG is obtained by using a standard 12-lead arrangement, but it can be obtained by using other lead systems including, for example, a 3-lead system.

When patients have myocardial ischemia or injury, an ST portion (discussed below) of the ECG signal in affected leads may deviate from an isoelectric line. The affected leads may indicate an ST elevation from the isoelectric line, and the reciprocal leads may indicate ST depression from the isoelectric line. Cardiologists quantify ST-segment resolution in the affected leads to identify which patients with ST elevation myocardial infarctions (STEMI) are at greater risk and may need more aggressive intervention.

In one embodiment disclosed herein, an automated method is used to quantify and display ST-segment resolution in affected ECG leads. The method provides for the automation and presentation of a user selected baseline ST-segment measurement, an elapsed time per ECG lead from the baseline measurement to a user selected percentage of ST-segment resolution (e.g., time to 20%, 30%, 50% and/or 70% ST-segment resolution), and/or a percent ST-segment resolution per ECG lead at a user selected time (e.g., at 30, 60, 90, and/or 180 minutes) following measurement of the selected baseline. The user (e.g., clinician) may select which of these measures to display. For example, the user may select to view an elapsed time to 50% ST-segment resolution on a linear graphical trend, and/or the percentage ST-segment resolution at 60 minutes.

In one embodiment, a method for dynamically monitoring ST-segment resolution in a patient includes acquiring an ECG signal that includes, for each of a plurality of detected heart beats, an ST-segment between a QRS complex and a T wave.

The method further includes, at a user selected time, determining a baseline value for the ST-segment relative to an isoelectric value, measuring a plurality of ST-segment values relative to the isoelectric value for a plurality of heart beats over time, and displaying a linear graphical trend of variations in the measured ST-segment values relative to the baseline value. In certain embodiments, the method also includes detecting a trigger event relative to at least one of the user selected time and the baseline value, and providing indicia of the trigger event.

In addition, or in another embodiment, an audible annunciation is provided of percent ST-segment resolution from a baseline measurement. In a cardiac catheter laboratory ("cath lab"), for example, interventional cardiologists perform procedures such as coronary angiography that generally require a focus on the instrumentation of devices in the heart. For example, the cardiologist or other clinician may perform intermittent fluoroscopic visualization of heart chambers and vessels. Thus, monitoring of the ECG and other vital signs may be performed by other persons in the lab. The cardiologist, however, may desire to be quickly informed about acute changes in ST-segments. Thus, this embodiment provides annunciation of percent ST-segment resolution (e.g., of one or more selected leads) from baseline measurements.

In one embodiment, a method for monitoring ST-segment resolution in a patient includes acquiring a plurality of ECG signals from respective leads attached to a patient, each ECG signal including an ST-segment between a QRS complex and a T wave for each of a plurality of detected heart beats. For each lead, the method also includes determining a percent ST-segment resolution as compared to respective baseline values. The method further includes comparing each of the percent ST-segment resolutions to a threshold value, and (based on the comparison) providing a verbal annunciation of the percent ST-segment resolution values that meet or exceed the threshold value. The verbal annunciation may also include an identification of a corresponding lead for each percent ST-segment resolution value that meets or exceeds the threshold value. In certain embodiments, for each respective lead, the method includes displaying an overlapping baseline ECG signal and a current ECG signal. For each of the percent ST-segment resolution values that meets or exceeds the threshold value based on the comparison, the method may also include highlighting (e.g., enlarging) the respective display of the overlapping baseline ECG signal and the current ECG signal.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

FIG. 1 graphically represents a typical ECG signal 100 of a heart of a normal, healthy person and includes a P wave, a Q wave, an R wave, an S wave, and a T wave. The P wave represents atrial depolarization. The initial portion of the P wave is largely a reflection of right atrial depolarization and the terminal portion is largely a reflection of left atrial depolarization. When visible, the Q wave is any initial downward deflection after the P wave. The typical Q wave represents septal depolarization. The R wave is the first upward deflection after the P wave and represents early ventricular depolarization. The S wave is the first negative deflection after the R wave and represents late ventricular depolarization. The T wave is normally upright, somewhat rounded and slightly asymmetric. The T wave represents repolarization of the ventricles. A QRS complex 110 begins at the onset of the Q wave and ends at the endpoint of the S wave. The QRS complex 110 represents the duration of ventricular depolarization.

Generally, little or no electrical activity is visible along an isoelectric line 112 during a PR-segment 114 and an ST-segment 116 of the ECG signal 100. The PR-segment 114 begins at an endpoint of the P wave and ends at the onset of the QRS complex 110. The PR-segment 114 represents the time it takes for an electrical impulse to reach the ventricles from the A-V node. The ST-segment 116 begins at the endpoint of the S wave and ends at the onset of the T wave. During the ST-segment 116, the atrial cells are relaxed and the ventricles are contracted so that electrical activity may not be visible. In other words, as indicated above, the ST-segment 116 is normally isoelectric.

Figure 2A:
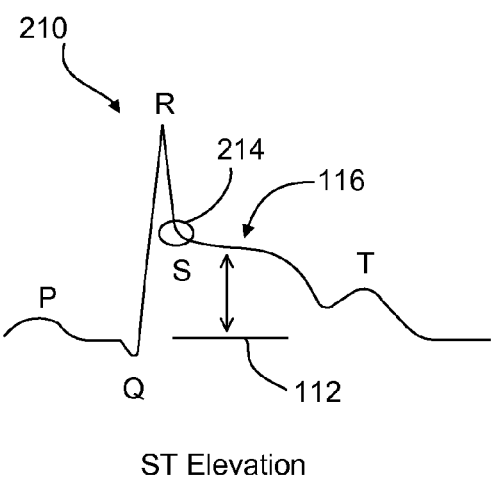
FIGS. 2A and 2B graphically represent respective ECG signals that differ from the typical ECG signal shown in FIG. 1.
Figure 2B:
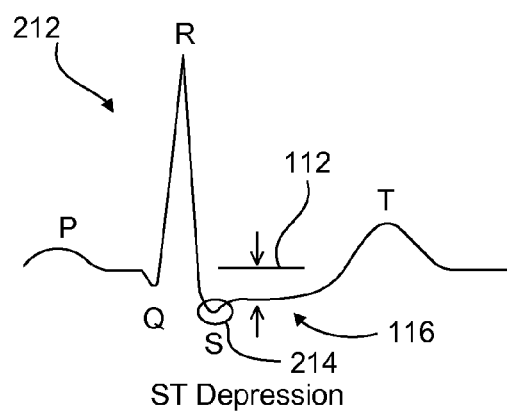

FIGS. 2A and 2B graphically represent respective ECG signals 210, 212 that differ from the "typical" ECG signal 100. As shown in FIGS. 2A and 2B, the ST-segment 116 may experience elevation (FIG. 2A) or depression (FIG. 2B) from the isoelectric line 112 in a vertical direction. ST-segment elevation or depression may occur, for example, with cardiac injury, ventricular aneurysms, Prinzmetals angina, pericarditis, myocardial ischemia, or other diseases. An artisan will recognize from the disclosure herein that ST elevation shown in FIG. 2A and the ST depression shown in FIG. 2B may occur in the same patient as detected through different leads.

FIGS. 2A and 2B also illustrate locations of respective J-points 214. The J-point 214 is a junction between the QRS complex 110 and the ST-segment 116. As discussed below, a selected time duration from the J-point is used to determine a location where the amplitude of the ST-segment is measured. For example, traditional ST-segment measurements may be made at approximately $\frac{1}{16} \times$R-R interval post J-point, where the R-R interval is the heart beat interval or distance between a selected point on one ECG signal to the corresponding point on the succeeding signal. This corresponds, for example, to a 60 msec post J-point time at a heart rate of approximately 60 beats per minute.

Figure 3:
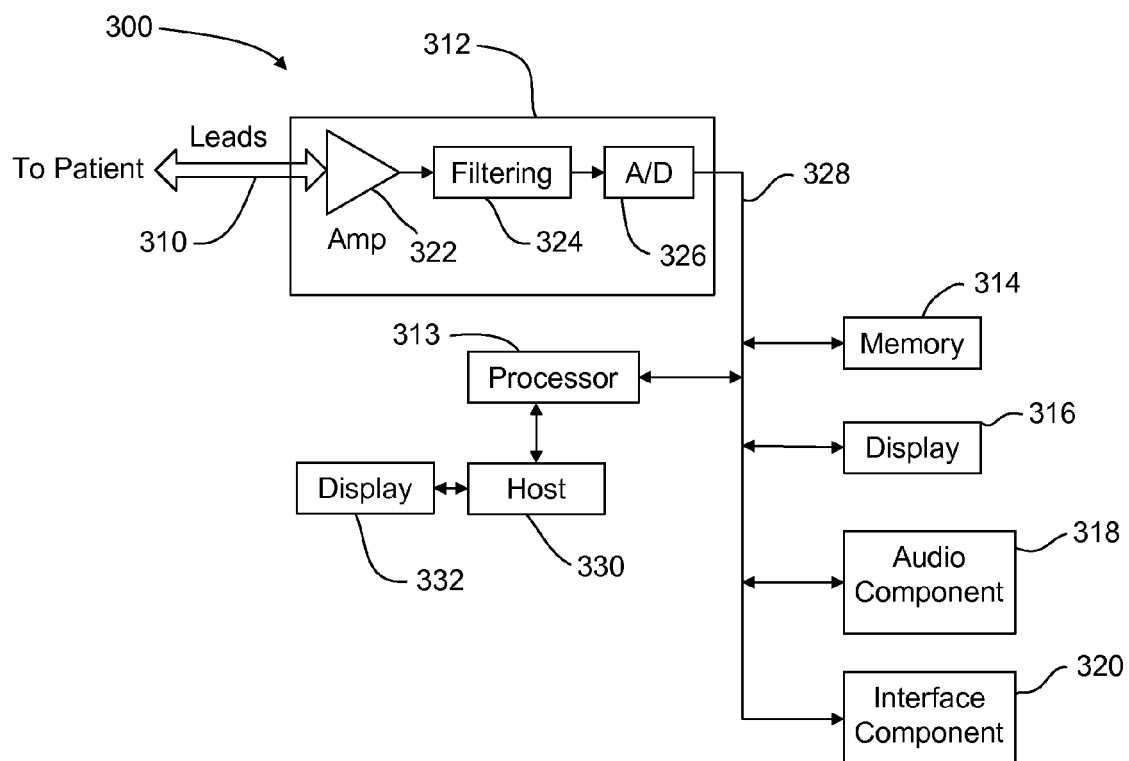
FIG. 3 is a simplified block diagram of a system for monitoring ST-segment resolution according to one embodiment.

FIG. 3 is a simplified block diagram of a system 300 for monitoring ST-segment resolution according to one embodiment. The system 300 includes a plurality of leads 310 electrically connected to a receiver component 312 that is in communication with a processor 313, a memory device 314, a display device 316, an audio component 318, and an interface component 320. The leads 310 include wires and electrodes configured to attach to a patient (not shown) to detect ECG signals. The receiver 312 may include, for example, an amplification component 322 to amplify the ECG signals detected by the leads 310, a filtering component 324 to eliminate undesirable noise from the ECG signals, and an analog-to-digital (A/D) converter 326 to provide converted ECG signals through a system bus 328 to the processor 313.

The processor 313 may include a special purpose processor configured to perform the processes described herein. In another embodiment, the processor 313 is a general purpose processor configured to execute computer executable instructions (e.g., stored in the memory device 314) to perform the processes described herein. In addition, or in other embodiments, the processor 313 may be connected to a host computer 330 having a display device 332. The host computer 330 may include computer executable instructions for performing the processes described herein. The host computer 330 may be used in certain embodiments, for example, to provide remote patient monitoring.

In one embodiment, the system 300 allows a clinician to select one or more indicators of myocardial reflow for use in guiding a patient's therapy. The system then automatically monitors and displays the selected indicators on at least one of the display devices 316, 332. In certain embodiments, the audio component 318 provides an audible alarm and/or verbal annunciation of ST-segment resolution percentages that exceed a defined threshold. The interface component 320 may include, for example, an integrated keypad, touch screen, or other user controls. The interface component 320 may also include, for example, interfaces for an external keyboard, a mouse, a printer, an external storage device, and/or a network adapter.

In one embodiment, a clinician may press a key, for example, to manually mark the ST-segments (from available ECG leads) as baseline measurements. The clinician may also mark the ST-segments at the initiation of an intervention and enter text that describes the marker (e.g. "baseline" or "thrombolytic"). The system 300 monitors the patient and automatically displays the clinician selected indicators of ST-segment change in the ECG leads that meet predefined or selected measurement criteria.

Figures 4, 5:
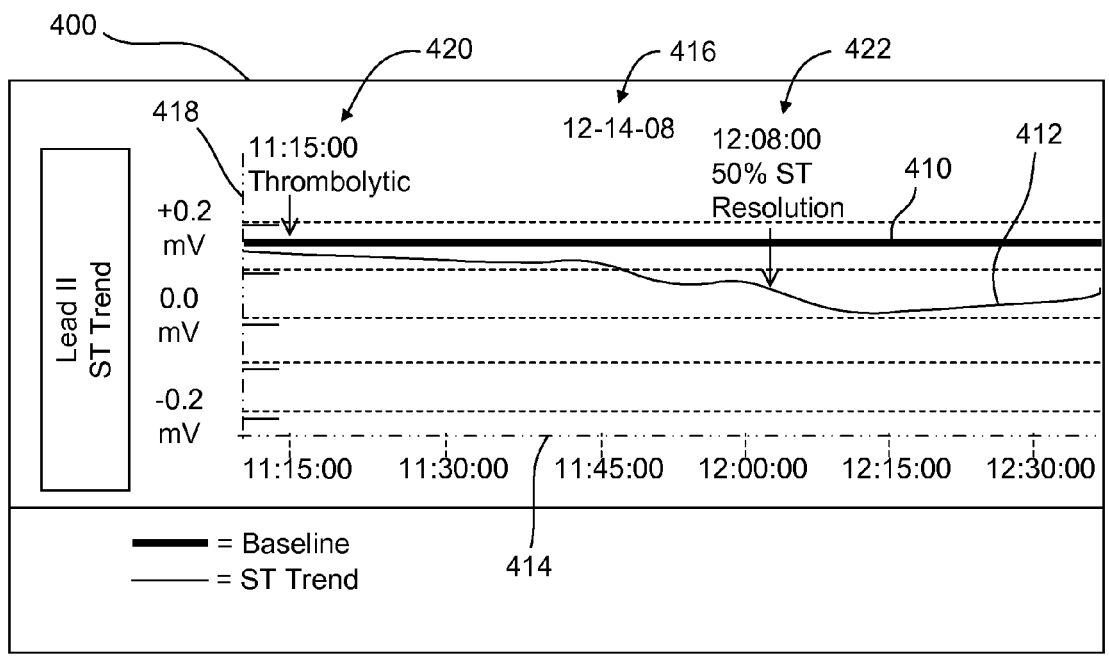
FIG. 4 graphically illustrates a user interface for displaying a linear graphical trend of an ST-segment in a selected lead according to one embodiment.
FIG. 5 graphically illustrates a user interface for displaying percent ST-segment resolution values per ECG lead at predetermined or user selected times according to one embodiment.

FIG. 4 graphically illustrates a user interface 400 for displaying a linear graphical trend of an ST-segment in a selected lead according to one embodiment. The user interface 400 may be displayed, for example, on the system display device 316 and/or the host display device 332 shown in FIG. 3. The user interface 400 graphically displays a baseline value 410 of the ST-segment relative to the ST trend 412, which corresponds to variations in the ST-segment over time. Thus, the user may quickly compare the historical ST-segment value with the baseline ST-segment value.

As shown in FIG. 4, the ST trend 412 may be plotted relative to time displayed in an x-axis 414. The time displayed in the x-axis 414 may be an actual time of day (e.g. 11:15:00, 11:30:00, 11:45:00 . . . ) on a displayed date 416 or an elapsed time relative to measuring the baseline value 410 and/or treating the patient. The ST trend 412 may also be plotted relative to a measured voltage value displayed in a y-axis 418. Thus, using the values displayed in the x-axis 414 and the y-axis 418, the user may quickly determine the numerical value of the ST-segment at a selected point in time. The user may also quickly determine a percentage of ST-segment resolution.

In one embodiment, the user interface 400 automatically displays one or more markers that indicate a time to reach a trigger event such as a predetermined or user selected ST-segment resolution threshold. For example, the user interface 400 may display markers relative to the ST trend 412 to indicate when 20%, 30%, 50%, and/or 70% ST-segment resolution is reached for the selected lead.

In the example shown in FIG. 4, a first marker 420 corresponds to an intervention and includes an arrow at the time of the intervention, a displayed time of day when the intervention was administered to the patient, and user entered text to indicate the type of intervention (e.g. a "thrombolytic" was administered at 11:15:00). A second marker 422 corresponds to the trigger event and includes an arrow at the time of the trigger event, a time of the trigger event and text describing the trigger event (e.g., 50% ST-segment resolution was reached at 12:08:00). Thus, the user is visually notified that the time to 50% ST-segment resolution for lead II is 53 minutes. In certain embodiments, the audio component 318 provides an audible alarm (e.g., a tone or verbal announcement, as discussed below) when a trigger event is detected.

Although a single trigger event marker 422 (50% ST-segment resolution) is displayed in FIG. 4, an artisan will recognize from the disclosure herein that multiple trigger event markers may also be displayed (e.g., for 20%, 30%, 50%, and/or 70% ST-segment resolution). Further, multiple linear graphical trends 412 corresponding to various affected leads may be displayed together. An artisan will also recognize from the disclosure herein that other types of markers and/or information may also be displayed including, for example, an elapsed time between measuring the baseline value and administering the intervention, an elapsed time between measuring the baseline value and the second marker 422, an elapsed time between the first marker 420 and the second marker 422, shapes other than arrows, the ST-segment value and/or percent of ST-segment resolution at the time of the first marker 420, and colors to distinguish between various markers.

FIG. 5 graphically illustrates a user interface 500 for displaying percent ST-segment resolution values per ECG lead at predetermined or user selected times according to one embodiment. The user interface 500 may be displayed, for example, on the system display device 316 and/or the host display device 332 shown in FIG. 3. In certain embodiments, the user interface 500 may be displayed in addition to the user interface 400 shown in FIG. 4.

The predetermined or user selected times displayed in the user interface 500 may be relative to the baseline measurement time and/or the intervention time. Thus, the user may quickly determine quantitative values for affected leads at various times. In the example shown in FIG. 5, numeric percentage values for ST-segment resolution are provided for lead II, lead III, and lead AVF at 30 minutes, 60 minutes, 90 minutes, and 180 minutes. An artisan will recognize from the disclosure herein that any lead may be selected for display of its percent ST-segment resolution.

Figure 6:
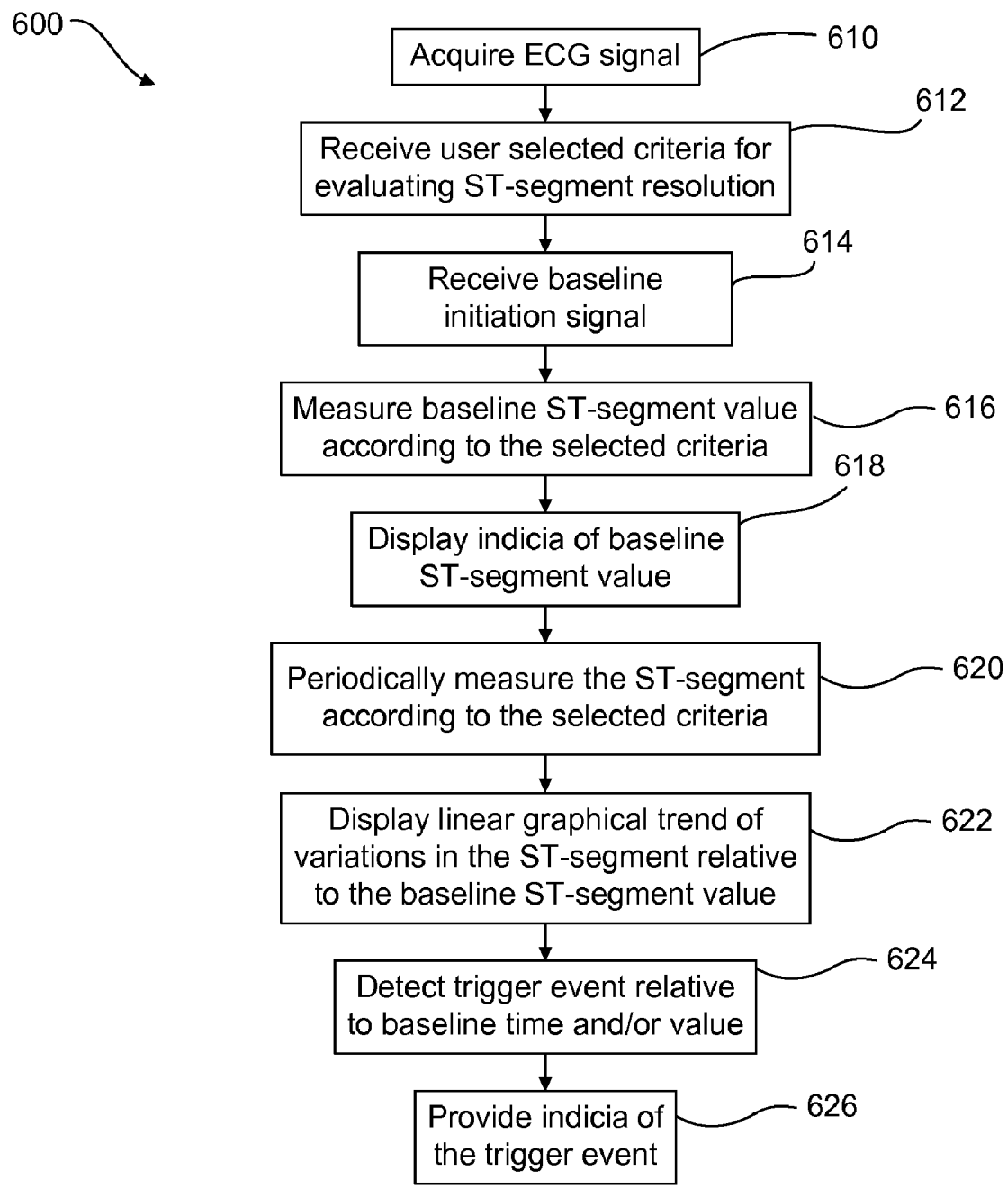
FIG. 6 is a flow chart illustrating a method for dynamically monitoring ST-segment resolution in a patient according to one embodiment.

FIG. 6 is a flow chart illustrating a method 600 for dynamically monitoring ST-segment resolution in a patient according to one embodiment. The method 600 includes acquiring 610 an ECG signal and receiving 612 user selected criteria for evaluating ST-segment resolution. As discussed in detail below with respect to FIGS. 7A and 7B, the criteria for evaluating the ST-segment resolution may include a user selected post J-point time at which the system 300 measures successive ST-segment values, or defining parameters for using multiple post J-point times to statistically analyze ST-segment changes (e.g., by determining variance, skew, kurtosis, and/or other characteristics of data points measured within the ST-segment). The criteria for evaluating ST-segment resolution may also include display options, alarm options, and trigger event options. The system may include a set of default criteria for evaluating the ST-segment. The user may also be allowed to define one or more of the default criteria.

The method 600 also includes receiving 614 a baseline initiation signal, measuring 616 a baseline ST-segment value according to the selected criteria in response to the baseline initiation signal, and displaying 618 indicia of the baseline ST-segment value. In one embodiment, the baseline initiation signal is activated when the ECG signal is first detected and the criteria for evaluating the ST-segment resolution are known. In addition, or in other embodiments, the baseline initiation signal is set by the user to reset the baseline at a desired time (e.g., at a time corresponding to a treatment administered to the patient). A time at which the baseline ST-segment value is measured may be referred to herein as a "baseline time." As shown in FIG. 4, the indicia of the baseline ST-segment value may include a horizontal line 412 and/or a marker 420.

The method 600 includes periodically measuring 620 the ST-segment deviation according to the selected criteria and displaying 622 a linear graphical trend of variations in the ST-segment deviation relative to the baseline ST-segment value. The ST-segment values may be measured, for example, every heartbeat (e.g., every detected J-point 214), a selected fraction of the heartbeats (e.g., every fourth detected J-point 214), or at selected or predetermined intervals (e.g., approximately every 90 msec). As discussed above, an example linear graphical trend 412 of variations in the ST-segment relative to the baseline ST-segment value 410 is shown in FIG. 4.

The method 600 may also include detecting 624 a trigger event relative to the baseline time and/or value and providing 626 indicia of the trigger event. As discussed above, the trigger event may include detecting a selected or predetermined percentage of ST-segment resolution (e.g., upon detecting 20%, 30%, 50%, and/or 70% ST-segment resolution). The trigger event may also correspond to a selected or predetermined time after the baseline time (e.g., 30 minutes, 60 minutes, 90 minutes, and/or 180 minutes after the baseline time).

The method 600 shown in FIG. 6 may be used, for example, when a patient is in a hospital's emergency department with chest pain, being monitored in a coronary care unit while receiving intravenous fibrinolytics or other interventions, in a telemetry unit being monitored via a wireless transmitter to a central station monitor, or during a catheterization procedure in the catheterization lab. Busy healthcare providers may forget to measure and calculate the ST-segment changes at appropriate times. Further, there may be different levels of expertise wherein not all personnel are trained to make ST-segment resolution measurements. Thus, an automated technique such as the method 600 shown in FIG. 6 advantageously standardizes and systematically implements a protocol in an emergency department, coronary care unit, or other treatment facility. Such a method provides selected, institutionally accepted measurements that automatically appear on the patient's monitor and/or central station when a trigger event is detected, indicating a selected magnitude of ST-segment resolution. This data may be accessible at any time on the patient's monitor and/or the central monitoring system.

Figure 7A:
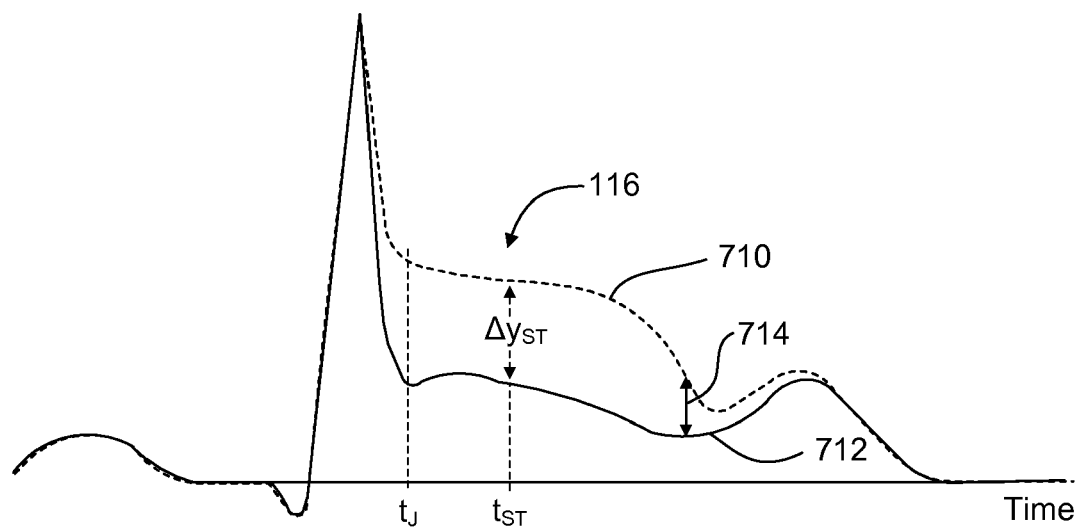
FIG. 7A graphically represents using a selected post J-point time in an ST-segment to evaluate ST-segment resolution according to one embodiment.

FIG. 7A graphically represents the use of a selected post J-point time $t_{ST}$ in an ST-segment 116 to evaluate ST-segment resolution according to one embodiment. For illustrative purposes a baseline ECG signal 710 (dashed line) is shown overlapping a current ECG signal 712 (solid line) with the peak values of the respective R waves aligned. In one embodiment, known techniques are used to automatically determine and track the J-point time $t_J$ of the respective ECG signals 710, 712. A user may select a post J-point time $t_{ST}$ (e.g., 20 msec, 40 msec, 60 msec, 80 msec) at which a height difference $\Delta y_{ST}$ between the baseline ECG signal 710 and the current ECG signal 712 is determined. A cardiologist or other skilled health care provider may select the post J-point time $t_{ST}$ based on factors such as the patient's heart rate.

Selection of the post J-point time $t_{ST}$ may have a drastic affect on the ST-segment resolution value. For example, if the post J-point time $t_{ST}$ were selected such that it were in an area 714 closer to the T wave, the change in height $\Delta y_{ST}$ between the baseline ECG signal 710 and the current ECG signal 712 would be much less than that shown in FIG. 7A. In other words, not every point within the ST-segment 116 will likely reach a selected ST-segment resolution (e.g., 50%) at the same time. Thus, in certain embodiments, multiple post J-point times are used to evaluate ST-segment resolution.

Figure 7B:
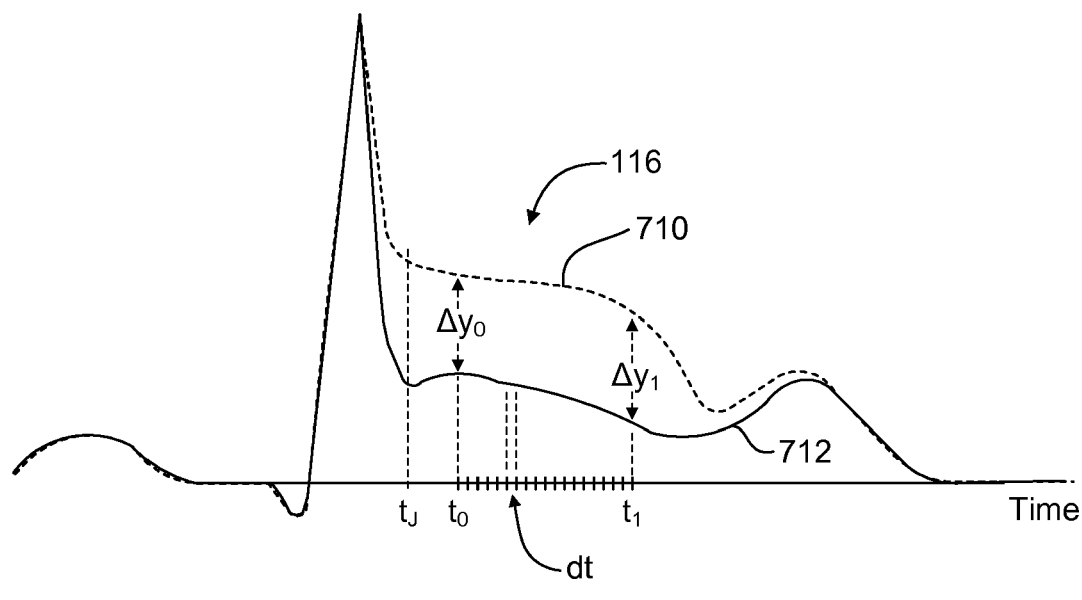
FIG. 7B graphically represents using multiple post J-point times in an ST-segment to evaluate ST-segment resolution according to another embodiment.

For example, FIG. 7B graphically represents using multiple post J-point times in an ST-segment 116 to evaluate ST-segment resolution according to another embodiment. In this example, ST-segment values are measured at multiple post J-point times beginning with an initial time $t_0$ and a final time $t_1$. The distance between post J-point times is represented by dt. An artisan will recognize from the disclosure herein that any number of post J-point times within the ST-segment 116 may be used, and may be limited in certain embodiments only by the speed at which the data points may be measured. Between the initial time $t_0$ and the final time $t_1$, the difference between the baseline ECG signal 710 and the current ECG signal 712 varies between $\Delta y_0$ and $\Delta y_1$.

Various techniques may be used to evaluate changes in measured data sets corresponding to the baseline ECG signal 710 and the current ECG signal 712. For example, integration techniques may be used to determine the area between the baseline ECG signal 710 and the current ECG signal 712 during the interval from the initial time $t_0$ and the final time $t_1$. In another embodiment, a trigger may be detected when any of the measured points between the initial time $t_0$ and the final time $t_1$ reaches a selected threshold value (e.g., 50% resolution).

In addition, or in another embodiment, various statistical techniques may be used such as comparing the mean value or standard deviation of the baseline data set to the mean value or standard deviation of the current data set. Another statistical technique may include comparing the variance or distribution spread of the data sets about their respective mean values by calculating the second moment of the respective data sets. In addition, or in another embodiment, the skew or lack of symmetry may be compared by calculating the third moment of the respective data sets. In addition, or in another embodiment, the kurtosis or degree to which the distribution is peaked may be compared by calculating the fourth moment of the respective data sets. An artisan will recognize from the disclosure herein that many other known statistical techniques may be used to evaluate changes to the ST-segment 116 over time.

In certain embodiments, audible alarms and/or other audible indications are automatically provided when a threshold ST-segment resolution value is reached on one or more leads. For example, in one embodiment, verbal annunciation of percent ST-segment resolution of one or more selected leads is provided when a user selected percent ST-segment resolution is detected. For example, if the user selects notification when the ST-segment percent resolution is greater than or equal to 20%, the system 300 shown in FIG. 3 may announce, "33% ST-segment resolution in Lead V1 and 25% ST-segment resolution in Lead V2."

In addition to the annunciated quantitative ST changes, a visual comparison of the baseline ECG signals to current ECG signals is provided in certain such embodiments for some or all of the ECG leads. In some embodiments, ECG signals with ST-segment resolutions that reach the threshold, or ECG signals corresponding to selected leads, are automatically magnified or otherwise highlighted on the user interface. The user interface may display one baseline ECG signal (e.g., corresponding to a pre-intervention heart beat) using a first line color (or pattern) for each affected lead, superimposed with the current ECG signal of the same respective lead in a second line color (or pattern). Together with the quantitative ST-segment resolution, the visual ECG changes may be part of an ST report provided to the user.

Figure 8:
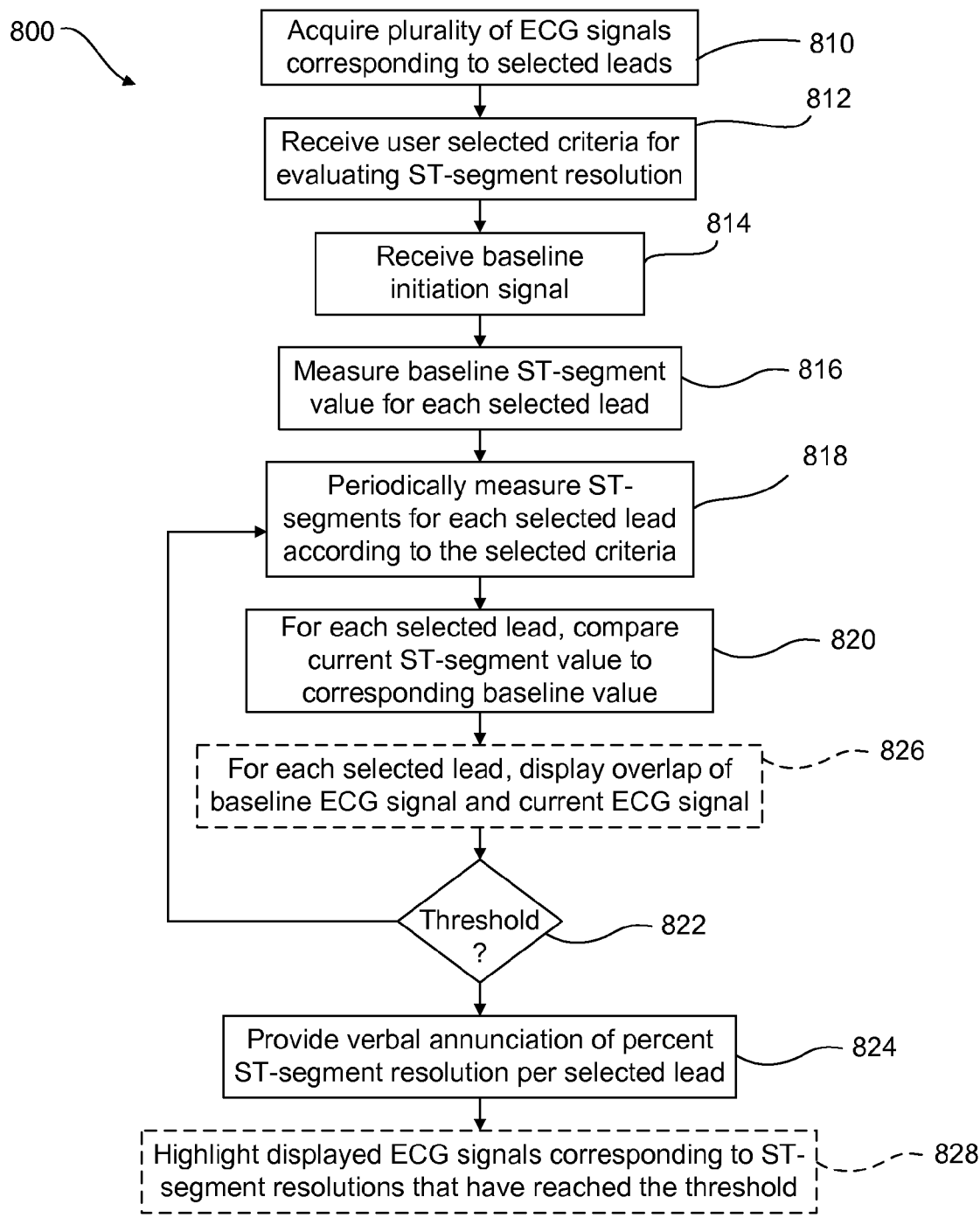
FIG. 8 is a flow chart illustrating a method for monitoring ST-segment resolution in a patient according to one embodiment.

FIG. 8 is a flow chart illustrating a method 800 for monitoring ST-segment resolution in a patient according to one embodiment. The method 800 shown in FIG. 8 includes acquiring 810 a plurality of ECG signals corresponding to selected leads, receiving 812 user selected criteria ST-segment resolution, receiving 814 a baseline initiation signal measuring 816 baseline ST-segment values for each selected lead, and periodically measuring 818 ST-segments for each selected lead according to the selected criteria.

For each selected lead, the method 800 further includes comparing 820 a current ST-segment value to the corresponding baseline value and querying 822 whether the ST-segment resolution for the lead has reached a threshold value. If none of the leads has reached the threshold ST-segment resolution value, the method 800 continues measuring 818 ST-segment for each selected lead and comparing 820 the current ST segment value to its corresponding baseline value. Once one or more leads reach the threshold ST-segment resolution value, the method 800 provides a verbal annunciation of percent ST-segment resolution per selected lead. In one embodiment, the annunciation (e.g., "50% ST-segment resolution in lead II") is provided for all selected leads. In another embodiment, the annunciation is only provided for leads that have reached the threshold value.

As shown in FIG. 8, in some embodiments the method 800 also includes, for each selected lead, displaying 826 an overlap of the baseline ECG signal and the current ECG signal. For example, FIG. 9A graphically illustrates a user interface 900 for displaying a plurality of overlapped ECG signals 910 (twelve overlapped pairs shown) according to one embodiment. In this example, current ECG signals are displayed as solid lines overlapped with their respective baseline ECG signals as dashed lines, for each lead (lead I, lead II, lead III, lead aVR, lead aVL, lead aVF, lead V1, lead V2, lead V3, lead V4, lead V5, and lead V6). The R wave of each current ECG signal is aligned with the R wave of its corresponding baseline ECG signal. In certain embodiments, different colors may be used for current ECG signals and baseline ECG signals.

Figure 9A:
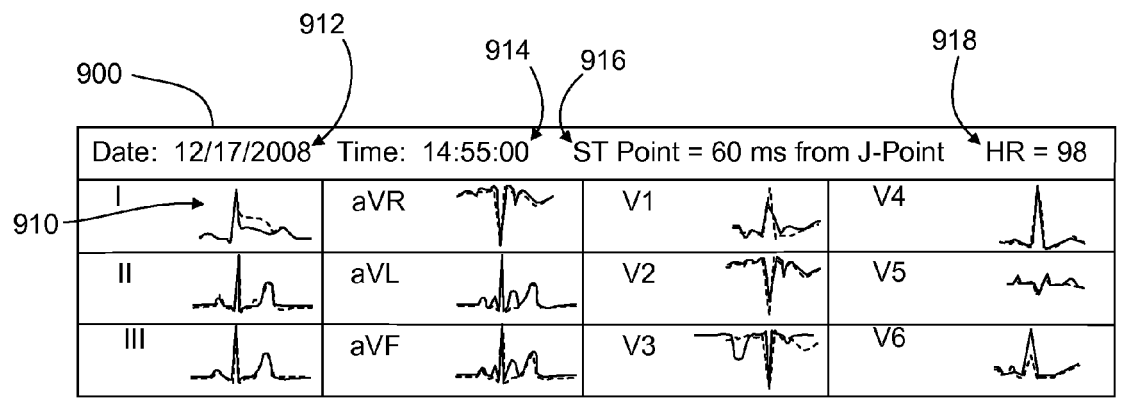
FIG. 9A graphically illustrates a user interface for displaying a plurality of overlapped ECG signals according to one embodiment.

While FIG. 9A shows overlapped ECG signals 910 for each lead in a twelve-lead system, in certain embodiments a user may select a subset of leads to display. As shown in FIG. 9A, the user interface 900 may include other information such as a current date 912, a current time 914, selected criteria for measuring ST-segments (e.g., measuring each ST-segment at a post J-point time of approximately 60 ms), and a current heart rate 918. An artisan will recognize that the user interface 900 may also display other information such as a baseline ST-segment value per lead, a current ST-segment value per lead, and/or a percent ST-segment resolution per lead.

Figure 9B:
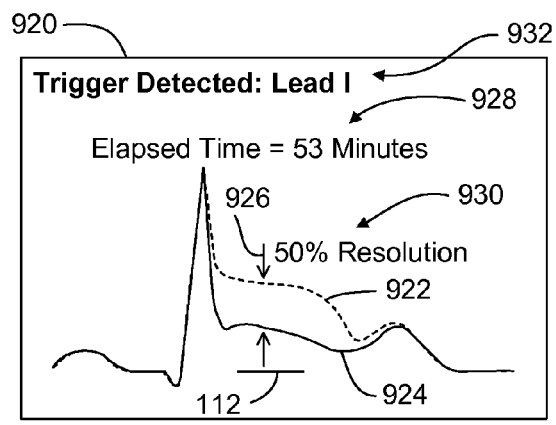
FIG. 9B graphically illustrates a user interface that displays an enlarged version of a baseline ECG signal overlapping a current ECG signal according to one embodiment.

The method 800 may also include highlighting 828 displayed ECG signals corresponding to ST-segment resolutions that have reached the threshold. For example, in addition to (or instead of) displaying the user interface 900 shown in FIG. 9A, the method 800 may display an enlarged version of overlapped ECG signals 910 corresponding to leads with ST-segment resolutions that have reached the threshold. For example, FIG. 9B graphically illustrates a user interface 920 that displays an enlarged version of a baseline ECG signal 922 (dashed line) overlapping a current ECG signal 924 corresponding to a particular lead (e.g., lead I) that has reached an ST-segment resolution threshold according to one embodiment. The user interface 920 may display the location of the isoelectric line 112, a location 926 (e.g., selected post J-point value) where the ST-segment is measured, the percent ST-segment resolution 928 (e.g., 50%), an elapsed time 930 between the baseline ECG signal 922 and the current ECG signal 924 (e.g., 53 minutes), and an indication 932 of the corresponding lead (e.g., lead I).

The method 800 shown in FIG. 8 may be used, for example, in acute situations when users (e.g., clinicians) are performing procedures and have other concurrent tasks that may not allow the user to view and calculate ST-segment changes from the ECG waveform data.

FIG. 10 graphically illustrates a user interface menu 1000 usable with the system 300 shown in FIG. 3 according to one embodiment. The user selectable functions discussed below with respect to the user interface menu 1000 may include software menu items (e.g., selectable with a mouse), dedicated controls (e.g., front panel controls), keystrokes on a keyboard, and/or other user interactions.

The user interface menu 1000 allows a user to select a "set baseline" function 1010 to reset the ST-segment baseline for available ECG vectors (leads). When the user activates the set baseline function 1010, selected ECG waveforms and corresponding ST-segment numeric data are bookmarked for later comparisons. In one embodiment, bookmarking includes recording the selected waveforms for a predetermined amount of time. For example, in one embodiment, selecting the set baseline function 101 records the selected ECG waveforms and corresponding ST-segment values for a minimum approximately six seconds. An artisan will understand from the disclosure herein, however, that much shorter or much longer times may also be used.

The user interface menu 1000 also allows the user to select a "relearn baseline" function 1012 that causes the current ECG complex from each available lead to become the most recently learned baseline morphology. The ST-segment values from each ECG lead (e.g., deviations from the isoelectric line) become the baseline numeric values and the point from which high and low alarm limits trigger the ST alarm annunciation.

In one embodiment, the user interface menu 1000 also allows the user to select an "ST-segment measurement criteria" function 1014. As discussed above, the user may specify when each ST-segment measurement is to be carried out and/or define statistical measurements for evaluating ST-segment resolution. In one embodiment, the system 300 is configured to dynamically analyze ST-segment deviation with variations in heart rate. Using known algorithms, the system 300 provides accurate ST-segment measurements without constant user surveillance to reposition the isoelectric line, J-point value, and/or post-J point value. The algorithms are also used to automatically measure ST-segment values by determining the vertical distance from the isoelectric line to the post J-point measurement location.

In addition, or in other embodiments, the user may select the post J-point value from a menu. For example, FIG. 11 graphically illustrates a user menu 1100 for selecting a post J-point value according to one embodiment. The user menu 1100 allows a user to select, for example, a 20 msec, 30 msec, 40 msec, 60 msec, or 80 msec post J-point value. The user menu 1100 also allows the user to make a "custom selection" to enter a desired post J-point value that is not listed in the menu. In certain embodiments, the system 300 automatically places a post J-point cursor at the selected time for measuring ST-segments, until such time as the user may change the post J-point duration. In one embodiment, the system 300 provides a warning to the user when the ECG complex does not allow sufficiently accurate ST-segment measurements when relatively long post J-point durations are selected (e.g., when a high heart rate causes the selected post J-point to be located proximate to or within the T wave).

In addition, or in other embodiments, the ST-segment measurement criteria function 1014 may allow the user to select from various statistical analysis options for multiple data points acquired within the ST-segments. For example, as discussed above, the user may select comparisons based on variance, skew, kurtosis, or other statistical analysis functions. The user may also be allowed to define parameters to use in the statistical analysis such as start and stop times within the ST-segment, and distances between acquired data points.

In one embodiment, the user interface menu 1000 allows the user to select a "freeze" function 1016 to hold the display of a current ECG signal. In certain such embodiments, the user is allowed to position electronic cursors or calipers on the display screen to manually measure the ST-segment elevation or depression.

In one embodiment, the user interface menu 1000 allows the user to select an "ST presentation options" function 1018 that provides the user with the ability to select from a variety of two-beat superimposition options. For example, FIG. 12 graphically illustrates a user menu 1200 for selecting ST presentation options according to one embodiment. The options include displaying baseline ST values to current ST values, displaying baseline ST values to peak deviations, displaying baseline ST values to selected ST alarm events, displaying peak ST values to current ST values, displaying peak ST values to post-intervention ST values, displaying baseline ST values to 60 minutes post-intervention ST values, and displaying baseline ST values to 90 minutes post-intervention ST values. An artisan will recognize from the disclosure herein that other display options my also be available. In one embodiment, a default presentation includes displaying baseline ST values to current ST values.

Returning to FIG. 10, the user interface menu 1000 may also allow a user to select an "ST alarms" function 1020 that provides the user with the ability to select a percent ST-segment resolution threshold and/or a post-intervention time. When ST alarm limits are violated in one embodiment, for example, the user is able to quickly compare the baseline ST values to those leads which violated alarm limits, as discussed above in relation to FIGS. 9A and 9B.

The user interface menu 1000 may also allow a user to select a "mark event" function 1022 that provides the user with the ability to mark an event (bookmark) to indicate a time corresponding to an intervention (treatment) or patient symptom. As discussed above, the intervention may be labeled on available waveform data and trend data to correspond to the time of the marked event. The user is able to compare the baseline ECG values to the time at which an event was marked.

The user interface menu 1000 may also allow a user to select a "display leads" function 1024 that provides the user with the ability to group and display specific ECG leads (e.g., from a list of available leads for three, five, six, and ten-lead wire systems) per myocardial segment anatomy such as anterior, posterior, inferior, and lateral ventricular walls. For example, FIG. 13 graphically illustrates a user menu 1300 for selecting groups of leads for display according to one embodiment. In this example embodiment, grouped leads that may be selected for display correspond to inferior ischemia (leads I, II, and AVF), lateral ischemia (leads I, AVL, V5, and V6), septal ischemia (leads V1 and V2), posterior ischemia (leads V1, V2, and V3), and global ischemia (leads AVF, V2, and V6). The user interface also includes a "custom selection" option to selectively group any combination of leads for display.

It will be understood by those having skill in the art that many changes may be made to the details of the above-described embodiments without departing from the underlying principles of the invention. The scope of the present invention should, therefore, be determined only by the following claims.

The invention claimed is:

1. A system for dynamically monitoring ST-segment resolution in a patient, the system comprising:
   a receiver to acquire an electrocardiogram (ECG) signal through a plurality of leads, the ECG signal including, for each of a plurality of detected heart beats, an ST-segment between a QRS complex and a T wave;
   a processor to process the ECG signal to determine values for the ST-segment relative to an isoelectric value;
   one or more controls to provide a user selected baseline signal to the processor, the processor responding to the baseline signal by marking a baseline ST-segment value corresponding to a baseline time; wherein the one or more controls further allow the user to select criteria for evaluating ST-segment resolution, wherein the processor determines the values for the ST-segment based on the user selected criteria, and wherein the user-selected criteria further comprises one or more statistical algorithms selected from the group comprising mean, standard deviation, variance, skew, and kurtosis; and
   a user interface in communication with the processor to display a linear graphical trend of variations in the measured ST-segment values relative to the baseline ST-segment value.

2. The system of claim 1, wherein the processor is further configured to:
   detect a trigger event relative to at least one of the baseline time and the baseline ST-segment value; and
   provide indicia of the trigger event.

3. The system of claim 2, wherein the trigger event comprises an ST-segment resolution percentage reaching a threshold value.

4. The system of claim 3, wherein the indicia of the trigger event comprises a marker displayed at a location on the linear graphical trend corresponding to an elapsed time when the ST-segment resolution percentage reaches the threshold, wherein the marker indicates the elapsed time and the ST-segment resolution percentage.

5. The system of claim 3, further comprising an audio component to provide an audible signal for the indicia of the trigger event.

6. The system of claim 5, wherein the audible signal comprises a verbal annunciation that communicates the ST-segment resolution percentage.

7. The system of claim 6, wherein the verbal annunciation further communicates an identification of a lead that acquired the ECG signal.

8. The system of claim 2, wherein the trigger event comprises a lapse of a predetermined amount of time after a user-selected time.

9. The system of claim 8, wherein the indicia of the trigger event comprises a display of a measured percentage ST-segment resolution value on the user interface for one or more leads relative to the lapsed time.

10. A system for dynamically monitoring ST-segment resolution in a patient, the system comprising:
 a receiver to acquire an electrocardiogram (ECG) signal through a plurality of leads, the ECG signal including, for each of a plurality of detected heart beats, an ST-segment between a QRS complex and a T wave;
 a processor to process the ECG signal to determine values for the ST-segment relative to an isoelectric value;
 one or more controls to provide a user selected baseline signal to the processor, the processor responding to the baseline signal by marking a baseline ST-segment value corresponding to a baseline time; wherein the one or more controls further allow the user to select criteria for evaluating ST-segment resolution, wherein the processor determines the values for the ST-segment based on the user-selected criteria, wherein the user-selected criteria comprise a post J-point value at which the processor determines the values for the ST-segment; and
 a user interface in communication with the processor to display a linear graphical trend of variations in the measured ST-segment values relative to the baseline ST-segment value.

11. A system for dynamically monitoring ST-segment resolution in a patient, the system comprising:
 a receiver to acquire an electrocardiogram (ECG) signal through a plurality of leads, the ECG signal including, for each of a plurality of detected heart beats, an ST-segment between a QRS complex and a T wave;
 a processor to process the ECG signal to determine values for the ST-segment relative to an isoelectric value;
 one or more controls to provide a user selected baseline signal to the processor, the processor responding to the baseline signal by marking a baseline ST-segment value corresponding to a baseline time; wherein the one or more controls further allow the user to select criteria for evaluating ST-segment resolution, wherein the processor determines the values for the ST-segment based on the user-selected criteria, and wherein the user-selected criteria comprise selection of multiple post J-point values; and
 a user interface in communication with the processor to display a linear graphical trend of variations in the measured ST-segment values relative to the baseline ST-segment value.

12. A system for dynamically monitoring ST-segment resolution in a patient, the system comprising:
 a receiver to acquire an electrocardiogram (ECG) signal through a plurality of leads, the ECG signal including, for each of a plurality of detected heart beats, an ST-segment between a QRS complex and a T wave;
 a processor to process the ECG signal to determine values for the ST-segment relative to an isoelectric value;
 one or more controls to provide a user selected baseline signal to the processor, the processor responding to the baseline signal by marking a baseline ST-segment value corresponding to a baseline time; and
 a user interface in communication with the processor to display a linear graphical trend of variations in the measured ST-segment values relative to the baseline ST-segment value;
 wherein the processor is further configured to:
  detect a trigger event relative to at least one of the baseline time and the baseline ST-segment value, wherein the trigger event comprises an ST-segment resolution percentage reaching a threshold value; and
  provide indicia of the trigger event, wherein the indicia of the trigger event comprises a marker displayed at a location on the linear graphical trend corresponding to an elapsed time when the ST-segment resolution percentage reaches the threshold, wherein the marker indicates the elapsed time and the ST-segment resolution percentage.

13. A system for dynamically monitoring ST-segment resolution in a patient, the system comprising:
 a receiver to acquire an electrocardiogram (ECG) signal through a plurality of leads, the ECG signal including, for each of a plurality of detected heart beats, an ST-segment between a QRS complex and a T wave;
 a processor to process the ECG signal to determine values for the ST-segment relative to an isoelectric value;
 one or more controls to provide a user selected baseline signal to the processor, the processor responding to the baseline signal by marking a baseline ST-segment value corresponding to a baseline time; and
 a user interface in communication with the processor to display a linear graphical trend of variations in the measured ST-segment values relative to the baseline ST-segment value;
 wherein the processor is further configured to:
  detect a trigger event relative to at least one of the baseline time and the baseline ST-segment value, wherein the trigger event comprises an ST-segment resolution percentage reaching a threshold value; and
  provide indicia of the trigger event, wherein the system further comprises an audio component to provide an audible signal for the indicia of the trigger event, and wherein the audible signal comprises a verbal annunciation that communicates the ST-segment resolution percentage.

14. The system of claim 13, wherein the verbal annunciation further communicates an identification of a lead that acquired the ECG signal.

* * * * *